US012295677B2

(12) United States Patent
Cascarano et al.

(10) Patent No.: US 12,295,677 B2
(45) Date of Patent: *May 13, 2025

(54) END-EFFECTORS FOR SURGICAL ROBOTIC SYSTEMS HAVING SEALED OPTICAL COMPONENTS

(71) Applicant: GLOBUS MEDICAL, INC., Audubon, PA (US)

(72) Inventors: James Cascarano, Cambridge, MA (US); Justin Larson, Reading, MA (US); Zachary Olenio, Derry, NH (US); Sritam Parashar Rout, Dracut, MA (US); Norbert Johnson, North Andover, MA (US)

(73) Assignee: Globus Medical, Inc., Audubon, PA (US)

( * ) Notice: Subject to any disclaimer, the term of this patent is extended or adjusted under 35 U.S.C. 154(b) by 350 days.

This patent is subject to a terminal disclaimer.

(21) Appl. No.: 17/540,602

(22) Filed: Dec. 2, 2021

(65) Prior Publication Data

US 2022/0087756 A1  Mar. 24, 2022

Related U.S. Application Data

(63) Continuation of application No. 16/193,447, filed on Nov. 16, 2018, now Pat. No. 11,278,360.

(51) Int. Cl.
*A61B 34/30* (2016.01)
*B25J 15/00* (2006.01)
(Continued)

(52) U.S. Cl.
CPC ............ *A61B 34/30* (2016.02); *B25J 15/0019* (2013.01); *B25J 19/021* (2013.01);
(Continued)

(58) Field of Classification Search
CPC ............ A61B 34/30; A61B 2034/2057; A61B 2034/2072; A61B 2090/3983;
(Continued)

(56) References Cited

U.S. PATENT DOCUMENTS

| 4,150,293 A | 4/1979 | Franke |
| 5,246,010 A | 9/1993 | Gazzara et al. |

(Continued)

FOREIGN PATENT DOCUMENTS

| CN | 104582622 A | 4/2015 |
| CN | 106236262 A | 12/2016 |

(Continued)

OTHER PUBLICATIONS

US 8,231,638 B2, 07/2012, Swarup et al. (withdrawn)

*Primary Examiner* — Amanda K Hulbert
*Assistant Examiner* — Natasha Patel

(57) ABSTRACT

An end-effector for a surgical robot system may include an end-effector body and an optical sub-assembly. The optical sub-assembly may include a housing coupled to the end-effector body, the housing including a threaded portion. The optical sub-assembly may further include a window that is transparent to a predetermined range of light radiation wavelengths. The optical sub-assembly may further include a gasket disposed between the housing and the window. The optical sub-assembly may further include a threaded ring disposed over the window and threadedly engaging the threaded portion of the housing, the threaded ring compressing the gasket between the window and the housing to form a seal between the window and the housing. The optical sub-assembly may further include a light emitter configured to emit light in the predetermined range of light radiation wavelengths through the window.

17 Claims, 7 Drawing Sheets

(51) Int. Cl.
*B25J 19/02* (2006.01)
*A61B 34/20* (2016.01)
*A61B 90/00* (2016.01)

(52) U.S. Cl.
CPC ............... *A61B 2034/2057* (2016.02); *A61B 2034/2072* (2016.02); *A61B 2090/3983* (2016.02)

(58) Field of Classification Search
CPC ......... A61B 90/37; A61B 5/064; A61B 90/11; A61B 2090/3945; A61B 34/20; A61B 2034/2055; A61B 2090/3979; A61B 90/39; A61B 2090/061; A61B 2090/067; A61B 2090/0813; A61B 2090/0818; A61B 34/70; A61B 2034/2065; B25J 15/0019; B25J 19/021
See application file for complete search history.

(56) References Cited

U.S. PATENT DOCUMENTS

| | | |
|---|---|---|
| 5,354,314 A | 10/1994 | Hardy et al. |
| 5,366,178 A | 11/1994 | Hsiong et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |

(56) References Cited

U.S. PATENT DOCUMENTS

| | | |
|---|---|---|
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Akin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,172,434 B1 | 5/2012 | Olsson |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jenser |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Arkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |

(56) References Cited

U.S. PATENT DOCUMENTS

| | | | |
|---|---|---|---|
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Voll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Issacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |

(56) References Cited

U.S. PATENT DOCUMENTS

| | | | |
|---|---|---|---|
| 9,814,535 B2 | 11/2017 | Bar et al. | |
| 9,820,783 B2 | 11/2017 | Donner et al. | |
| 9,833,265 B2 | 11/2017 | Donner et al. | |
| 9,848,922 B2 | 12/2017 | Tohmeh et al. | |
| 9,925,011 B2 | 3/2018 | Gombert et al. | |
| 9,931,025 B1 | 4/2018 | Graetzel et al. | |
| 10,034,717 B2 | 7/2018 | Miller et al. | |
| 2001/0034530 A1 | 10/2001 | Malackowski et al. | |
| 2001/0036302 A1 | 11/2001 | Miller | |
| 2002/0035321 A1 | 3/2002 | Bucholz et al. | |
| 2003/0153904 A1 | 8/2003 | Patel | |
| 2004/0068172 A1 | 4/2004 | Nowinski et al. | |
| 2004/0073279 A1* | 4/2004 | Malackowski | A61B 90/98 607/88 |
| 2004/0076259 A1 | 4/2004 | Jensen et al. | |
| 2004/0238763 A1 | 12/2004 | Wood | |
| 2005/0096502 A1 | 5/2005 | Khalili | |
| 2005/0143651 A1 | 6/2005 | Verard et al. | |
| 2005/0171558 A1 | 8/2005 | Abovitz et al. | |
| 2005/0228266 A1* | 10/2005 | McCombs | A61B 34/74 600/407 |
| 2006/0100610 A1 | 5/2006 | Wallace et al. | |
| 2006/0173329 A1 | 8/2006 | Marquart et al. | |
| 2006/0184396 A1 | 8/2006 | Dennis et al. | |
| 2006/0241416 A1 | 10/2006 | Marquart et al. | |
| 2006/0291612 A1 | 12/2006 | Nishide et al. | |
| 2007/0015987 A1 | 1/2007 | Benlloch Baviera et al. | |
| 2007/0021738 A1 | 1/2007 | Hasser et al. | |
| 2007/0038059 A1 | 2/2007 | Sheffer et al. | |
| 2007/0073133 A1 | 3/2007 | Schoenefeld | |
| 2007/0156121 A1 | 7/2007 | Millman et al. | |
| 2007/0156157 A1 | 7/2007 | Nahum et al. | |
| 2007/0167712 A1 | 7/2007 | Keglovich et al. | |
| 2007/0233238 A1 | 10/2007 | Huynh et al. | |
| 2008/0004523 A1 | 1/2008 | Jensen | |
| 2008/0013809 A1 | 1/2008 | Zhu et al. | |
| 2008/0033283 A1 | 2/2008 | Dellaca et al. | |
| 2008/0046122 A1 | 2/2008 | Manzo et al. | |
| 2008/0082109 A1 | 4/2008 | Moll et al. | |
| 2008/0108912 A1 | 5/2008 | Node-Langlois | |
| 2008/0108991 A1 | 5/2008 | von Jako | |
| 2008/0109012 A1 | 5/2008 | Falco et al. | |
| 2008/0144906 A1 | 6/2008 | Allred et al. | |
| 2008/0151041 A1 | 6/2008 | Shafer et al. | |
| 2008/0161680 A1 | 7/2008 | von Jako et al. | |
| 2008/0161682 A1 | 7/2008 | Kendrick et al. | |
| 2008/0177203 A1 | 7/2008 | von Jako | |
| 2008/0214922 A1 | 9/2008 | Hartmann et al. | |
| 2008/0228068 A1 | 9/2008 | Viswanathan et al. | |
| 2008/0228196 A1 | 9/2008 | Wang et al. | |
| 2008/0235052 A1 | 9/2008 | Node-Langlois et al. | |
| 2008/0269596 A1 | 10/2008 | Revie et al. | |
| 2008/0287771 A1 | 11/2008 | Anderson | |
| 2008/0287781 A1 | 11/2008 | Revie et al. | |
| 2008/0300477 A1 | 12/2008 | Lloyd et al. | |
| 2008/0300478 A1 | 12/2008 | Zuhars et al. | |
| 2008/0302950 A1 | 12/2008 | Park et al. | |
| 2008/0306490 A1 | 12/2008 | Lakin et al. | |
| 2008/0319311 A1 | 12/2008 | Hamadeh | |
| 2009/0012509 A1 | 1/2009 | Csavoy et al. | |
| 2009/0030428 A1 | 1/2009 | Omori et al. | |
| 2009/0080737 A1 | 3/2009 | Battle et al. | |
| 2009/0185655 A1 | 7/2009 | Koken et al. | |
| 2009/0198121 A1 | 8/2009 | Hoheisel | |
| 2009/0216113 A1 | 8/2009 | Meier et al. | |
| 2009/0228019 A1 | 9/2009 | Gross et al. | |
| 2009/0259123 A1 | 10/2009 | Navab et al. | |
| 2009/0259230 A1 | 10/2009 | Khadem et al. | |
| 2009/0264899 A1 | 10/2009 | Appenrodt et al. | |
| 2009/0281417 A1 | 11/2009 | Hartmann et al. | |
| 2009/0285526 A1 | 11/2009 | Mikkelsen et al. | |
| 2010/0022874 A1 | 1/2010 | Wang et al. | |
| 2010/0033563 A1* | 2/2010 | Boehnlein | H04N 7/183 348/84 |
| 2010/0039506 A1 | 2/2010 | Sarvestani et al. | |
| 2010/0125286 A1 | 5/2010 | Wang et al. | |
| 2010/0130986 A1 | 5/2010 | Mailloux et al. | |
| 2010/0228117 A1 | 9/2010 | Hartmann | |
| 2010/0228265 A1 | 9/2010 | Prisco | |
| 2010/0249571 A1 | 9/2010 | Jensen et al. | |
| 2010/0274120 A1 | 10/2010 | Heuscher | |
| 2010/0280363 A1 | 11/2010 | Skarda et al. | |
| 2010/0331858 A1 | 12/2010 | Simaan et al. | |
| 2011/0022229 A1 | 1/2011 | Jang et al. | |
| 2011/0077504 A1 | 3/2011 | Fischer et al. | |
| 2011/0098553 A1 | 4/2011 | Robbins et al. | |
| 2011/0137152 A1 | 6/2011 | Li | |
| 2011/0213384 A1 | 9/2011 | Jeong | |
| 2011/0224684 A1 | 9/2011 | Larkin et al. | |
| 2011/0224685 A1 | 9/2011 | Larkin et al. | |
| 2011/0224686 A1 | 9/2011 | Larkin et al. | |
| 2011/0224687 A1 | 9/2011 | Larkin et al. | |
| 2011/0224688 A1 | 9/2011 | Larkin et al. | |
| 2011/0224689 A1 | 9/2011 | Larkin et al. | |
| 2011/0224825 A1 | 9/2011 | Larkin et al. | |
| 2011/0230967 A1 | 9/2011 | O'Halloran et al. | |
| 2011/0238080 A1 | 9/2011 | Ranjit et al. | |
| 2011/0276058 A1 | 11/2011 | Choi et al. | |
| 2011/0282189 A1 | 11/2011 | Graumann | |
| 2011/0286375 A1 | 11/2011 | Schretter et al. | |
| 2011/0295062 A1 | 12/2011 | Gratacos Solsona et al. | |
| 2011/0295370 A1 | 12/2011 | Suh et al. | |
| 2011/0306986 A1 | 12/2011 | Lee et al. | |
| 2012/0035507 A1 | 2/2012 | George et al. | |
| 2012/0046668 A1 | 2/2012 | Gantes | |
| 2012/0051498 A1 | 3/2012 | Koishi | |
| 2012/0053597 A1 | 3/2012 | Anvari et al. | |
| 2012/0059248 A1 | 3/2012 | Holsing et al. | |
| 2012/0071753 A1 | 3/2012 | Hunter et al. | |
| 2012/0108923 A1 | 5/2012 | Cinbus et al. | |
| 2012/0108954 A1 | 5/2012 | Schulhauser et al. | |
| 2012/0136372 A1 | 5/2012 | Amat Girbau et al. | |
| 2012/0143084 A1 | 6/2012 | Shoham | |
| 2012/0184839 A1 | 7/2012 | Woerlein | |
| 2012/0197182 A1 | 8/2012 | Millman et al. | |
| 2012/0226145 A1 | 9/2012 | Chang et al. | |
| 2012/0235909 A1 | 9/2012 | Birkenbach et al. | |
| 2012/0245596 A1 | 9/2012 | Meenink | |
| 2012/0253332 A1 | 10/2012 | Moll | |
| 2012/0253360 A1 | 10/2012 | White et al. | |
| 2012/0256092 A1 | 10/2012 | Zingerman | |
| 2012/0294498 A1 | 11/2012 | Popovic | |
| 2012/0296203 A1 | 11/2012 | Hartmann et al. | |
| 2013/0006267 A1 | 1/2013 | Odermatt et al. | |
| 2013/0016889 A1 | 1/2013 | Myronenko et al. | |
| 2013/0030571 A1 | 1/2013 | Ruiz Morales et al. | |
| 2013/0035583 A1 | 2/2013 | Park et al. | |
| 2013/0060146 A1 | 3/2013 | Yang et al. | |
| 2013/0060337 A1 | 3/2013 | Petersheim et al. | |
| 2013/0094742 A1 | 4/2013 | Feilkas | |
| 2013/0096574 A1 | 4/2013 | Kang et al. | |
| 2013/0113791 A1 | 5/2013 | Isaacs et al. | |
| 2013/0116706 A1 | 5/2013 | Lee et al. | |
| 2013/0131695 A1 | 5/2013 | Scarfogliero et al. | |
| 2013/0144307 A1 | 6/2013 | Jeong et al. | |
| 2013/0158542 A1 | 6/2013 | Manzo et al. | |
| 2013/0165937 A1 | 6/2013 | Patwardhan | |
| 2013/0178867 A1 | 7/2013 | Farritor et al. | |
| 2013/0178868 A1 | 7/2013 | Roh | |
| 2013/0178870 A1 | 7/2013 | Schena | |
| 2013/0204271 A1 | 8/2013 | Brisson et al. | |
| 2013/0211419 A1 | 8/2013 | Jensen | |
| 2013/0211420 A1 | 8/2013 | Jensen | |
| 2013/0218142 A1 | 8/2013 | Tuma et al. | |
| 2013/0223702 A1 | 8/2013 | Holsing et al. | |
| 2013/0225942 A1 | 8/2013 | Holsing et al. | |
| 2013/0225943 A1 | 8/2013 | Holsing et al. | |
| 2013/0231556 A1 | 9/2013 | Holsing et al. | |
| 2013/0237995 A1 | 9/2013 | Lee et al. | |
| 2013/0245375 A1 | 9/2013 | DiMaio et al. | |
| 2013/0261640 A1 | 10/2013 | Kim et al. | |
| 2013/0272488 A1 | 10/2013 | Bailey et al. | |
| 2013/0272489 A1 | 10/2013 | Dickman et al. | |
| 2013/0274761 A1 | 10/2013 | Devengenzo et al. | |

(56) References Cited

U.S. PATENT DOCUMENTS

| | | |
|---|---|---|
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Avallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0165006 A1 | 6/2017 | Woods et al. |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0252114 A1 | 9/2017 | Crawford et al. |
| 2017/0258426 A1 | 9/2017 | Risher-Kelly et al. |
| 2017/0258535 A1 | 9/2017 | Crawford |
| 2017/0261196 A1 | 9/2017 | Chapman et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |
| 2018/0064497 A1 | 3/2018 | Hussain et al. |

FOREIGN PATENT DOCUMENTS

| | | |
|---|---|---|
| CN | 108368974 A | 8/2018 |
| JP | 2018161477 A | 10/2018 |

\* cited by examiner

END-EFFECTORS FOR SURGICAL ROBOTIC SYSTEMS HAVING SEALED OPTICAL COMPONENTS

CROSS-REFERENCE TO RELATED APPLICATIONS

The present application is a continuation of U.S. patent application Ser. No. 16/193,447, filed Nov. 16, 2018, which is incorporated herein in its entirety.

FIELD

The present disclosure relates to medical devices, and more particularly, end-effectors for surgical robotic systems having sealed optical components.

BACKGROUND

Position recognition systems for robot assisted surgeries are used to determine the position of and track a particular object in 3-dimensions (3D). In robot assisted surgeries, for example, certain objects, such as surgical instruments, need to be tracked with a high degree of precision as the instrument is being positioned and moved by a robot or by a physician, for example.

Infrared signal based position recognition systems may use passive and/or active sensors or markers for tracking the objects. In passive sensors or markers, objects to be tracked may include passive sensors, such as reflective spherical balls, which are positioned at strategic locations on the object to be tracked. Infrared transmitters transmit a signal, and the reflective spherical balls reflect the signal to aid in determining the position of the object in 3D. In active sensors or markers, the objects to be tracked include active infrared transmitters, such as light emitting diodes (LEDs), and thus generate their own infrared signals for 3D detection.

With either active or passive tracking sensors, the system then geometrically resolves the 3-dimensional position of the active and/or passive sensors based on information from or with respect to one or more of the infrared cameras, digital signals, known locations of the active or passive sensors, distance, the time it took to receive the responsive signals, other known variables, or a combination thereof.

These surgical systems can therefore utilize position feedback to precisely guide movement of robotic arms and tools relative to a patients' surgical site.

SUMMARY

According to some embodiments of inventive concepts, an end-effector for a surgical robot system may include an end-effector body configured to guide a surgical instrument. The end-effector may further include an optical sub-assembly coupled to the end-effector body. The optical sub-assembly may include a housing coupled to the end-effector body, the housing including an engagement portion. The optical sub-assembly may further include a window that is transparent to a predetermined range of light radiation wavelengths, the housing and the window forming a cavity. The optical sub-assembly may further include a gasket disposed between the housing and the window, the gasket defining a gasket hole therethrough. The optical sub-assembly may further include a cover portion disposed over the window and engaging the engagement portion of the housing, the cover portion compressing the gasket between the window and the housing to form a seal between the window and the housing, the cover portion defining a cover hole therethrough. The optical sub-assembly may further include a light emitter disposed in the cavity, the light emitter configured to emit light in the predetermined range of light radiation wavelengths through the gasket hole, the window, and the cover hole.

According to some other embodiments of inventive concepts, a surgical robot system is disclosed. The surgical robot system may include a robot base and an articulable robot arm coupled to the robot base. The surgical robot system may further include an end-effector coupled to the robot arm, wherein the robot arm is configured to selectively position the end-effector in a plurality of end-effector positions. The end-effector may include an end-effector body configured to guide a surgical instrument. The end-effector may further include an optical sub-assembly coupled to the end-effector body. The optical sub-assembly may include a housing coupled to the end-effector body, the housing comprising an engagement portion. The optical sub-assembly may further include a window that is transparent to a predetermined range of light radiation wavelengths, the housing and the window forming a cavity. The optical sub-assembly may further include a gasket disposed between the housing and the window, the gasket defining a gasket hole therethrough. The optical sub-assembly may further include a cover portion disposed over the window and engaging the engagement portion of the housing, the cover portion compressing the gasket between the window and the housing to form a seal between the window and the housing, the cover portion defining a cover hole therethrough. The optical sub-assembly may further include a light emitter disposed in the cavity, the light emitter configured to emit light in the predetermined range of light radiation wavelengths through the gasket hole, the window, and the cover hole. The optical sub-assembly may further include a processor circuit configured to determine, based on the light emitted by the light emitter of the optical sub-assembly, a particular one of the plurality of end-effector locations corresponding to a present location of the end-effector.

According to some other embodiments of inventive concepts, an end-effector for a surgical robot system is disclosed. The end-effector includes an end-effector body configured to guide a surgical instrument. The end-effector further includes an optical sub-assembly coupled to the end-effector body. The optical sub-assembly includes a housing coupled to the end-effector body, the housing comprising an engagement portion. The optical sub-assembly further includes a cover portion engaging the engagement portion of the housing. The optical sub-assembly further includes a gasket disposed between the housing and the cover portion, the gasket defining a gasket hole therethrough, the cover portion compressing the gasket between the cover portion and the housing to form a seal between the cover portion and the housing, the cover portion defining a cover hole therethrough. The optical sub-assembly further includes a light emitter disposed in the cavity, the light emitter configured to emit light in the predetermined range of light radiation wavelengths through the gasket hole and the cover hole.

Other methods and related surgical systems, and corresponding methods and computer program products according to embodiments of the inventive subject matter will be or become apparent to one with skill in the art upon review of the following drawings and detailed description. It is intended that all such surgical systems, and corresponding methods and computer program products be included within this description, be within the scope of the present inventive subject matter, and be protected by the accompanying claims. Moreover, it is intended that all embodiments disclosed herein can be implemented separately or combined in any way and/or combination.

BRIEF DESCRIPTION OF THE DRAWINGS

The accompanying drawings, which are included to provide a further understanding of the disclosure and are incorporated in a constitute a part of this application, illustrate certain non-limiting embodiments of inventive concepts. In the drawings.

DETAILED DESCRIPTION

Figure 1:
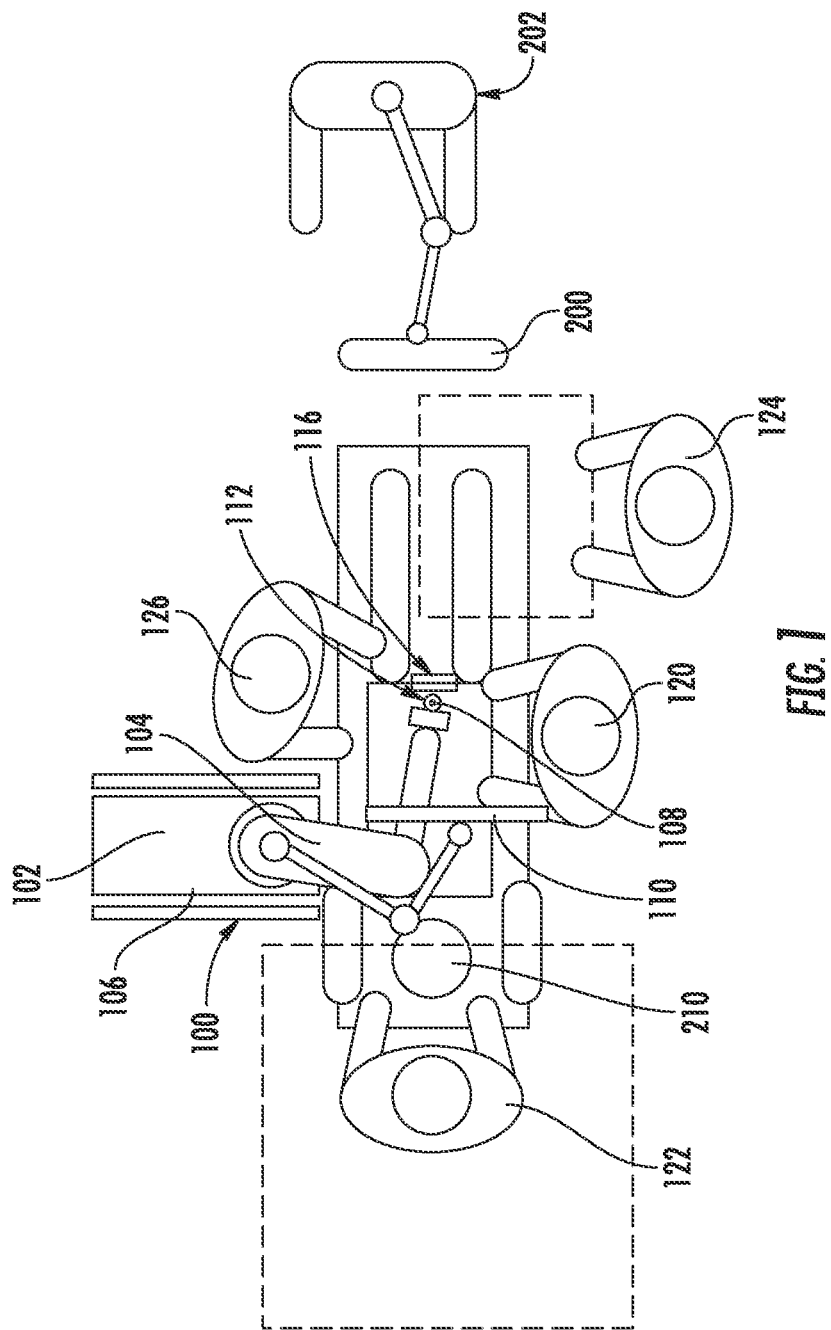
FIG. 1 is an overhead view of an arrangement for locations of a robotic system, patient, surgeon, and other medical personnel during a surgical procedure, according to some embodiments.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Figure 2:
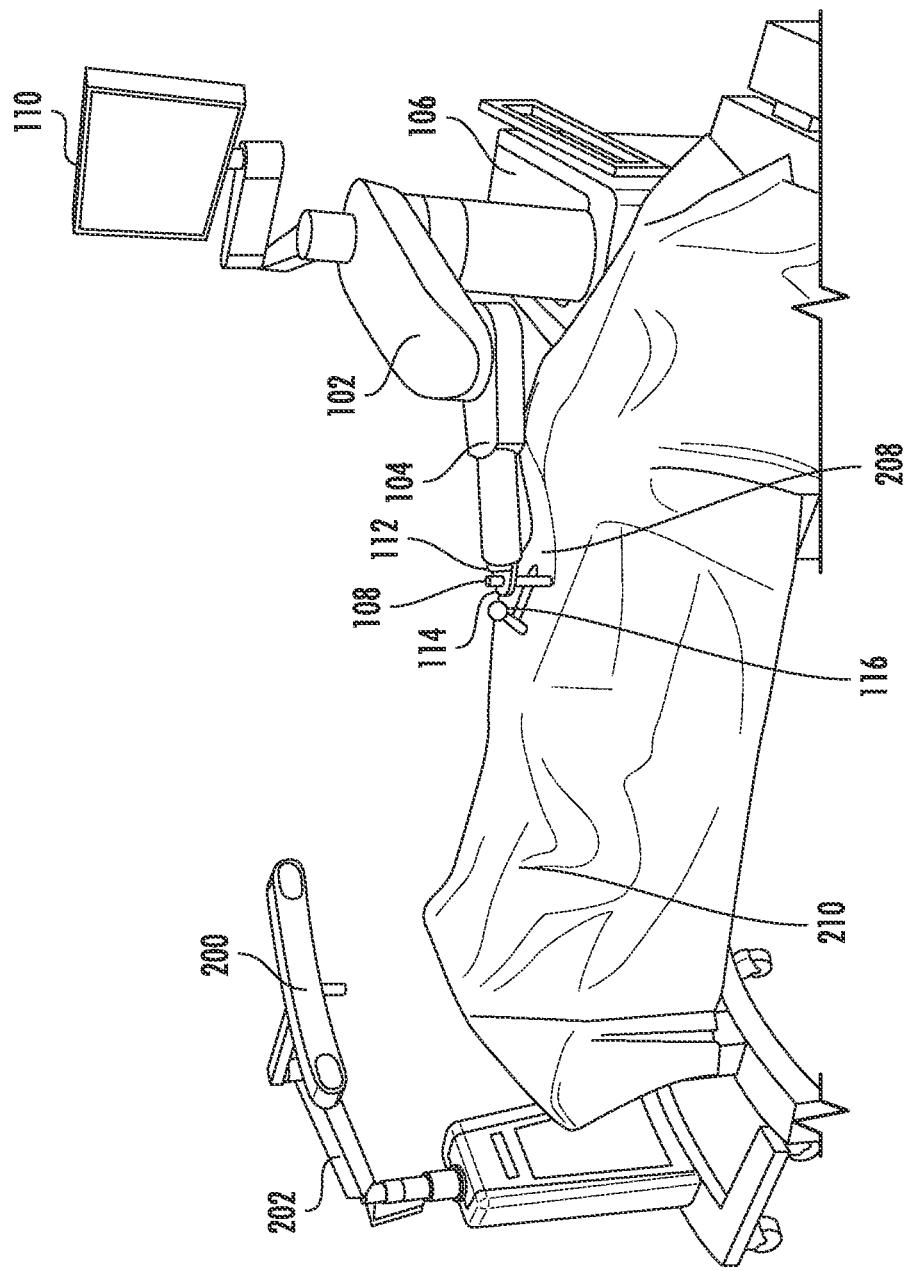
FIG. 2 illustrates a robotic system including positioning of the surgical robot and a camera relative to the patient according to some embodiments.

Turning now to the drawing, FIGS. 1 and 2 illustrate a surgical robot system 100 in accordance with an embodiment. Surgical robot system 100 may include, for example, a surgical robot 102, one or more robot arms 104, a base 106, a display 110, an end-effector 112, for example, including a guide tube 114, and one or more tracking markers 118. The surgical robot system 100 may include a patient tracking device 116 also including one or more tracking markers 118, which is adapted to be secured directly to the patient 210 (e.g., to a bone of the patient 210). The surgical robot system 100 may also use a sensor, such as a camera 200, for example, positioned on a camera stand 202. The camera stand 202 can have any suitable configuration to move, orient, and support the camera 200 in a desired position. The camera 200 may include any suitable camera or cameras, such as one or more infrared cameras (e.g., bifocal or stereophotogrammetric cameras), able to identify, for example, active and passive tracking markers 118 (shown as part of patient tracking device 116 in FIG. 2) in a given measurement volume viewable from the perspective of the camera 200. The camera 200 may scan the given measurement volume and detect the light that comes from the tracking markers 118 in order to identify and determine the position of the tracking markers 118 in three-dimensions. For example, active tracking markers 118 may include infrared-emitting markers that are activated by an electrical signal (e.g., infrared light emitting diodes (LEDs)), and/or passive tracking markers 118 may include retro-reflective markers that reflect infrared light (e.g., they reflect incoming IR radiation into the direction of the incoming light), for example, emitted by illuminators on the camera 200 or other suitable sensor or other device.

FIGS. 1 and 2 illustrate a potential configuration for the placement of the surgical robot system 100 in an operating room environment. For example, the robot 102 may be positioned near or next to patient 210. Although depicted near the head of the patient 210, it will be appreciated that the robot 102 can be positioned at any suitable location near the patient 210 depending on the area of the patient 210 undergoing the operation. The camera 200 may be separated from the surgical robot system 100 and positioned at the foot of patient 210. This location allows the camera 200 to have a direct visual line of sight to the surgical field 208. Again, it is contemplated that the camera 200 may be located at any suitable position having line of sight to the surgical field 208. In the configuration shown, the surgeon 120 may be positioned across from the robot 102, but is still able to manipulate the end-effector 112 and the display 110. A surgical assistant 126 may be positioned across from the surgeon 120 again with access to both the end-effector 112 and the display 110. If desired, the locations of the surgeon 120 and the assistant 126 may be reversed. The traditional areas for the anesthesiologist 122 and the nurse or scrub tech 124 may remain unimpeded by the locations of the robot 102 and camera 200.

With respect to the other components of the robot 102, the display 110 can be attached to the surgical robot 102 and in other embodiments, display 110 can be detached from surgical robot 102, either within a surgical room with the surgical robot 102, or in a remote location. End-effector 112 may be coupled to the robot arm 104 and controlled by at least one motor. In some embodiments, end-effector 112 can comprise a guide tube 114, which is able to receive and orient a surgical instrument 108 used to perform surgery on the patient 210. As used herein, the term "end-effector" is used interchangeably with the terms "end-effectuator" and "effectuator element." Although generally shown with a guide tube 114, it will be appreciated that the end-effector 112 may be replaced with any suitable instrumentation suitable for use in surgery. In some embodiments, end-effector 112 can comprise any known structure for effecting the movement of the surgical instrument 108 in a desired manner.

The surgical robot 102 is able to control the translation and orientation of the end-effector 112. The robot 102 is able to move end-effector 112 along x-, y-, and z-axes, for example. The end-effector 112 can be configured for selective rotation about one or more of the x-, y-, and z-axis, and a Z Frame axis (such that one or more of the Euler Angles (e.g., roll, pitch, and/or yaw) associated with end-effector 112 can be selectively controlled). In some embodiments, selective control of the translation and orientation of end-effector 112 can permit performance of medical procedures with significantly improved accuracy compared to conventional robots that use, for example, a six degree of freedom robot arm comprising only rotational axes. For example, the surgical robot system 100 may be used to operate on patient 210, and robot arm 104 can be positioned above the body of patient 210, with end-effector 112 selectively angled relative to the z-axis toward the body of patient 210.

In some embodiments, the position of the surgical instrument 108 can be dynamically updated so that surgical robot 102 can be aware of the location of the surgical instrument 108 at all times during the procedure. Consequently, in some embodiments, surgical robot 102 can move the surgical instrument 108 to the desired position quickly without any further assistance from a physician (unless the physician so desires). In some further embodiments, surgical robot 102 can be configured to correct the path of the surgical instrument 108 if the surgical instrument 108 strays from the selected, preplanned trajectory. In some embodiments, surgical robot 102 can be configured to permit stoppage, modification, and/or manual control of the movement of end-effector 112 and/or the surgical instrument 108. Thus, in use, in some embodiments, a physician or other user can operate the system 100, and has the option to stop, modify, or manually control the autonomous movement of end-effector 112 and/or the surgical instrument 108. Further details of surgical robot system 100 including the control and movement of a surgical instrument 108 by surgical robot 102 can be found in co-pending U.S. patent application Ser. No. 13/924,505, which is incorporated herein by reference in its entirety.

As will be described in greater detail below, the surgical robot system 100 can comprise one or more tracking markers configured to track the movement of robot arm 104, end-effector 112, patient 210, and/or the surgical instrument 108 in three dimensions. In some embodiments, a plurality of tracking markers can be mounted (or otherwise secured) thereon to an outer surface of the robot 102, such as, for example and without limitation, on base 106 of robot 102, on robot arm 104, and/or on the end-effector 112. In some embodiments, such as the embodiment of FIGS. 3A and 3B below, for example, one or more tracking markers can be mounted or otherwise secured to the end-effector 112. One or more tracking markers can further be mounted (or otherwise secured) to the patient 210. In some embodiments, the plurality of tracking markers can be positioned on the patient 210 spaced apart from the surgical field 208 to reduce the likelihood of being obscured by the surgeon, surgical tools, or other parts of the robot 102. Further, one or more tracking markers can be further mounted (or otherwise secured) to the surgical instruments 108 (e.g., a screw driver, dilator, implant inserter, or the like). Thus, the tracking markers enable each of the marked objects (e.g., the end-effector 112, the patient 210, and the surgical instruments 108) to be tracked by the robot 102. In some embodiments, system 100 can use tracking information collected from each of the marked objects to calculate the orientation and location, for example, of the end-effector 112, the surgical instrument 108 (e.g., positioned in the tube 114 of the end-effector 112), and the relative position of the patient 210. Further details of surgical robot system 100 including the control, movement and tracking of surgical robot 102 and of a surgical instrument 108 can be found in U.S. Patent Publication No. 2016/0242849, which is incorporated herein by reference in its entirety.

One drawback of conventional end-effectors is that it may be difficult to clean and sterilize the end-effector without damaging the components therein, including the markers on the end-effector and any internal electronic components of the end-effector. The robot base 106 and robot arm 104 may be isolated or shielded from the surgical environment, by a disposable plastic barrier (e.g., a cover or sleeve), for example, with the end-effector 112 attaching to an end of the robot arm 104 on the opposite side of the barrier, where the end-effector 112 may be exposed to bodily fluids, pathogens, or other contaminants during surgery. Following surgery, the end-effector 112 may be detached from the robot arm 104 for cleaning and/or sterilization, which may include a hot water soak and scrub, an ultrasonic bath, a spray rinse, and/or steam autoclave sterilization. Thus, there is a need for an end-effector design that is able to withstand these harsh conditions without sustaining damage to the end-effector or the components thereof.

Figure 3A:
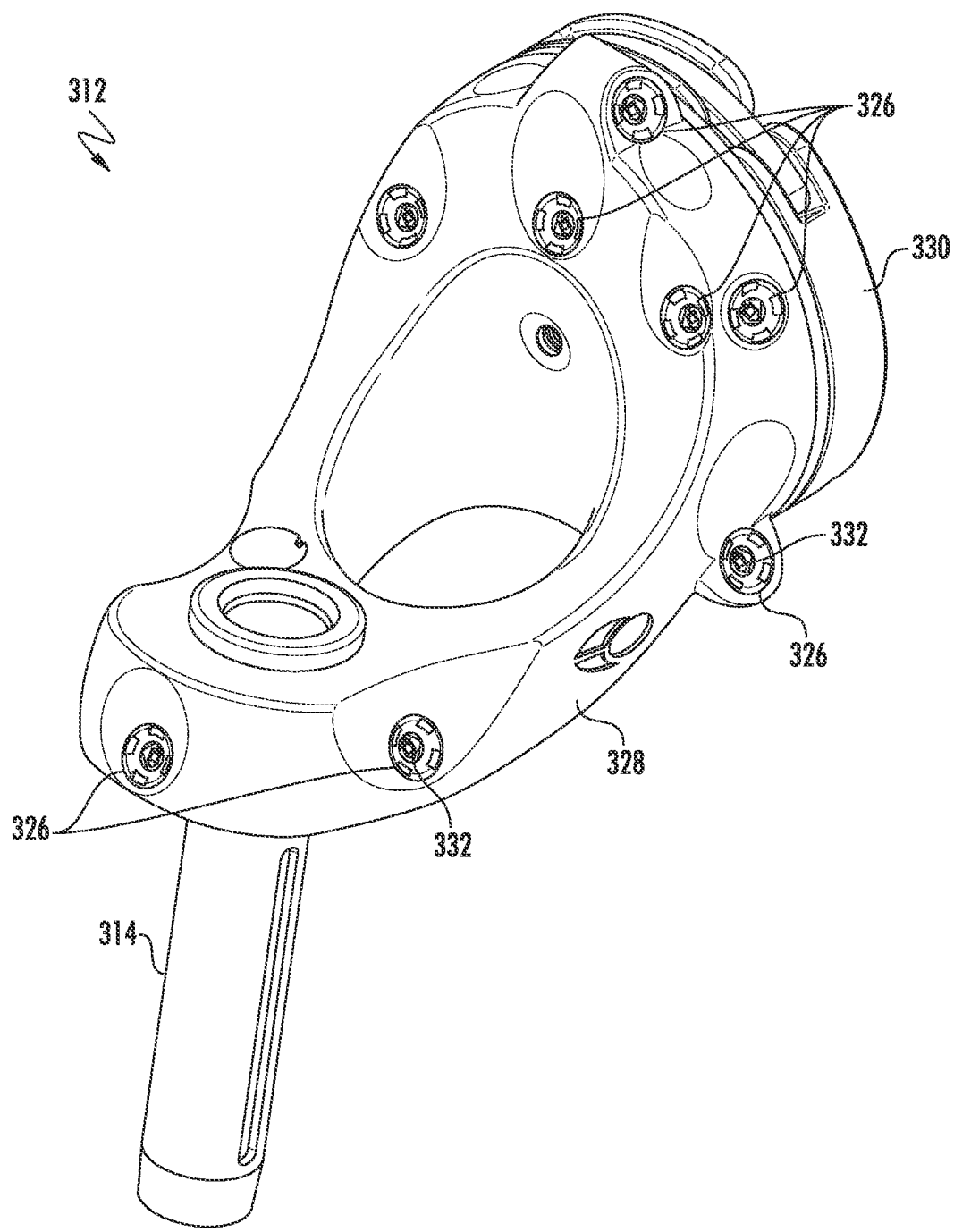
FIG. 3A illustrates an end-effector for use with a surgical robot system according to some embodiments.
Figure 3B:
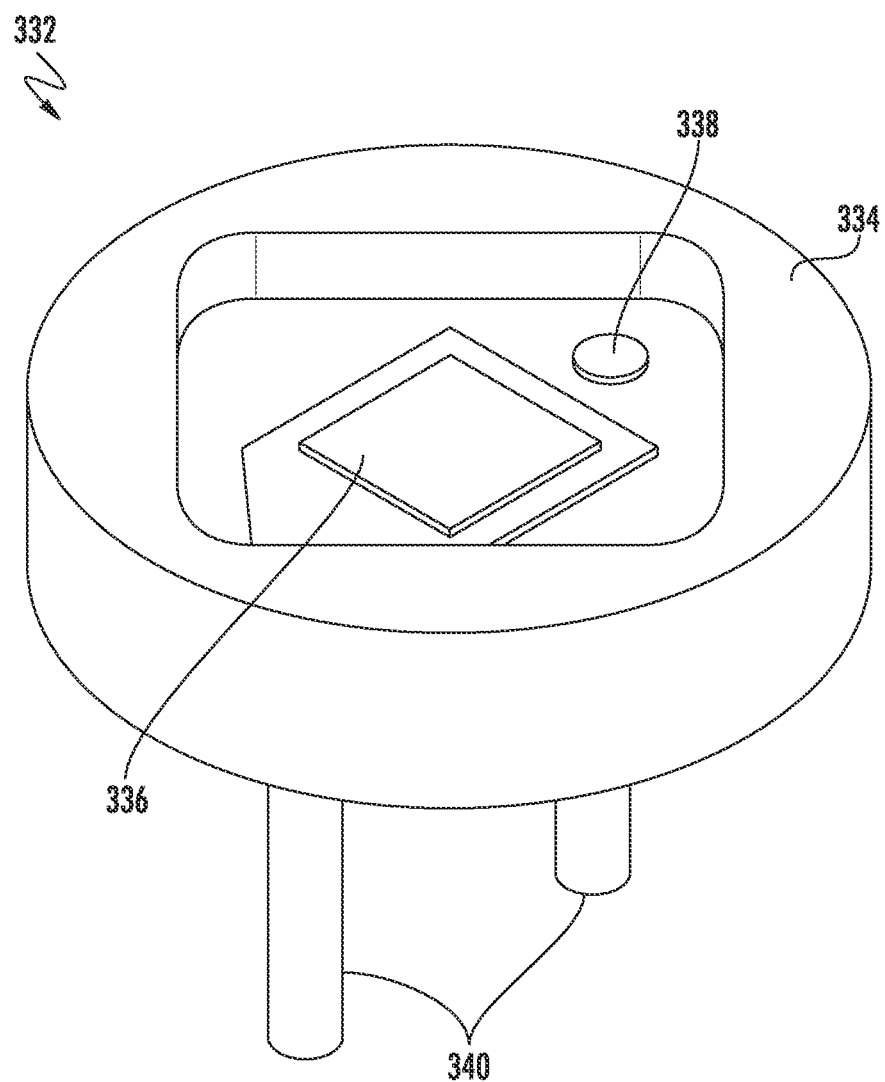
FIG. 3B illustrates an optical component of the end-effector of FIG. 3A for use in detecting a position of the end-effector relative to a patient, according to some embodiments.

Referring now to FIGS. 3A and 3B, an end-effector 312 having a plurality of tracking markers 326 for use with a surgical robot system is illustrated according to some embodiments. The end-effector 312 is similar to and may be used interchangeably with the end-effector 112 of FIGS. 1 and 2, according to some embodiments. In the embodiment of FIGS. 3A and 3B, the markers 326 include optical components 332 that include active infrared elements 336 (e.g., IR emitters and/or sensors), but it should be understood that other types of markers, such radiopaque or passive optical markers, may also be used. The markers 326 may be suitably shaped include spherical, spheroid, cylindrical, cube, cuboid, or the like. In some embodiments, one or more of markers 326 may be optical markers. In some embodiments, the positioning of one or more tracking markers 326 on end-effector 312 can maximize the accuracy of the positional measurements by serving to check or verify the position of end-effector 312.

Embodiments include one or more markers 326 coupled to the surgical instrument 108. In some embodiments, these markers 326, can comprise conventional infrared light-emitting diodes (LEDs) or an Optotrak® diode capable of being tracked using a commercially available infrared optical tracking system such as Optotrak®. Optotrak® is a registered trademark of Northern Digital Inc., Waterloo, Ontario, Canada. In other embodiments, markers 326 can comprise conventional reflective spheres capable of being tracked using a commercially available optical tracking system such as Polaris Spectra®. Polaris Spectra® is also a registered trademark of Northern Digital, Inc.

As discussed above, the markers 326 coupled to the end-effector 312 in this embodiment include active IR elements 336, which employ infrared light-emitting diodes which may be turned on and off. In some embodiments, light emitted from markers 326 (as well as light emitted or reflected from other markers, such as passive markers on a patient or instrument) can be detected by a camera, such as the camera 200 of FIGS. 1 and 2 for example, and can be used to monitor the location and movement of the end-effector 312 and other marked objects. In some alternative embodiments, markers 326 can include a radio-frequency and/or electromagnetic emitter, reflector and/or transceiver and the camera can include or be replaced by a radio-frequency and/or electromagnetic receiver and/or transceiver. In many embodiments, a camera or other end-effector sensor may detect the light emitted by the IR emitter and generate a location signal containing location information for the IR emitter.

As discussed above, the end-effector 312 may be exposed to harsh conditions during cleaning and/or sterilization, including extreme heat and/or moisture. One method of sealing and isolating the internal components of end-effectors includes disposing a potting material around the internal electronic components of the end-effector, such as the IR elements 336 of the markers 326, internal printed circuit assembly (PCA) (not shown), or other electronic components. The potting material may expand when exposed to heat, which may enhance the sealing properties of the potting material. However, this expansion may also result in physical damage to the internal components, such as solder joint fractures, for example, which may be compressed by the expanding potting material.

In the embodiment of FIGS. 3A and 3B, the end-effector 312 includes a body 328 that forms a guide tube 314 for retaining and/or orienting a surgical instrument, such as the surgical instrument 108 of FIGS. 1 and 2, for example. The end-effector 312 of FIGS. 3A and 3B also includes a mounting collar 330 for selectively coupling the end-effector 312 to a robot arm, such as the robot arm 104 of FIGS. 1 and 2, for example. Each of the plurality of optical components 332 includes an optical component housing 334, which may be separately formed from the end-effector body 328, or may be integrally formed with the end-effector body 328, as desired. Referring now to FIG. 3B, in addition or as an alternative to the IR element 336, which may allow the optical component 332 to emit IR light or detect or sense IR light being emitted by a different IR light source for example, the optical component 332 may also or alternatively includes one or more contact elements 338 (or other type of element), which may allow additional components to be connected to the optical component 332. The optical component 332 may also include electrical leads 340 for providing electrical power to and/or electrical signals to or from the optical component.

Figure 4A:
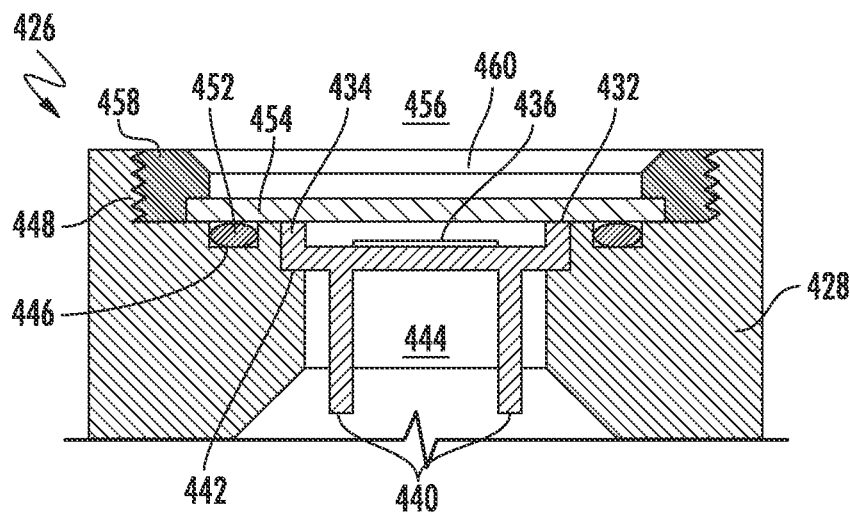
FIGS. 4A and 4B illustrate cross-sectional assembled and exploded views of a mounting arrangement for an optical component similar to the optical component of FIG. 3B in an end-effector similar to the end-effector of FIG. 3A, according to some embodiments.
Figure 4B:
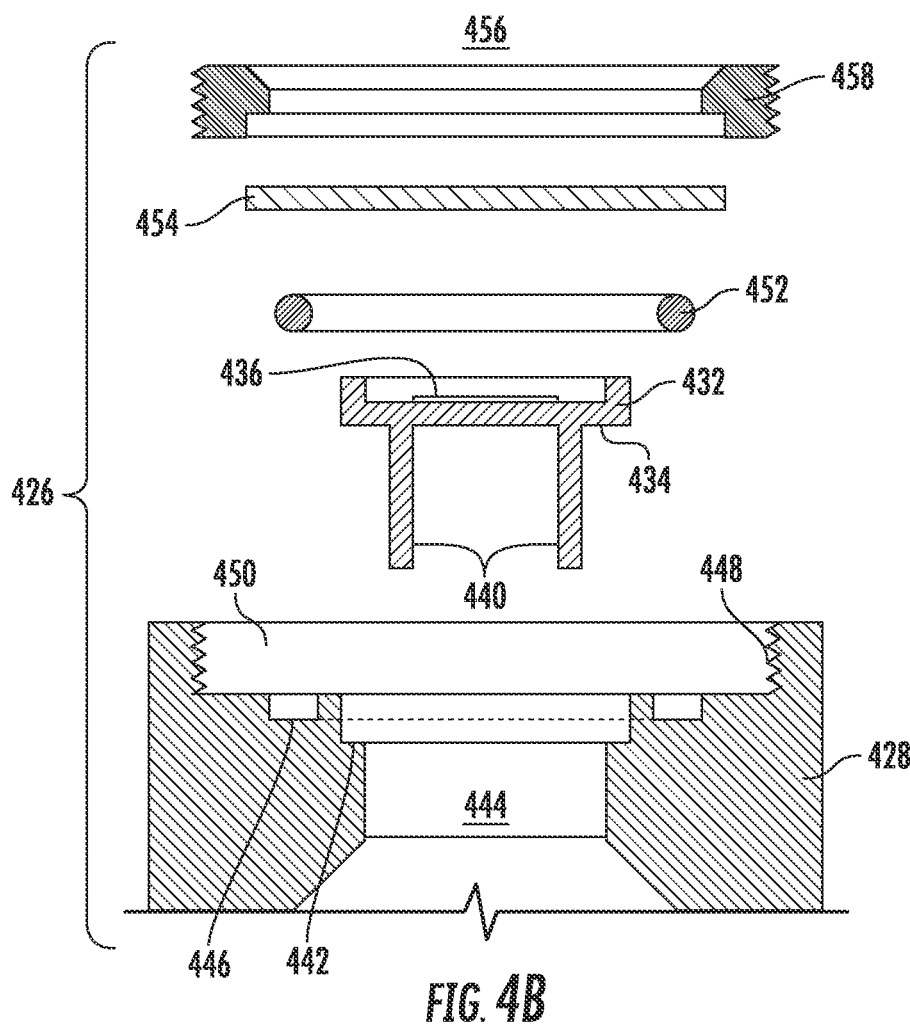

Referring now to FIGS. 4A and 4B, cross-sectional assembled and exploded views of a mounting arrangement for tracking marker 426 similar to the optical component 332 of FIG. 3B in an end-effector similar to the end-effector 312 of FIG. 3A is illustrated, according to some embodiments. The body 428 includes an optical component seat 442 for receiving and engaging the optical component housing 434 so that the leads 440 of the optical component 432 are disposed on an interior cavity 444 in the body 428. The body 428 of the tracking marker 426 also includes an O-ring seat 446, which is an annular cylindrical groove in this example. The body 430 of the tracking marker 426 also includes a threaded engagement portion 448, which includes inwardly facing threads to form a cylindrical recess 450 in the body 428 of the tracking marker 426 in this example.

To assemble the tracking marker 426, the optical component housing 434 is disposed in the component seat 442 of the body 428 of the tracking marker 426, and a compressible O-ring 452 is disposed in the O-ring seat 446. The O-ring 452 may be formed from any suitable material, such as rubber or another flexible or semi-flexible material, based on the material's ability to form a waterproof and/or moisture-proof seal, to withstand extreme temperatures, chemical exposure, or other properties of sterilization techniques, such as steam autoclave, hydrogen peroxide plasma or vapor, or ethylene oxide, for example. The O-ring 452 operates as a gasket in this embodiment, and it should be understood that other types of gaskets or other components may be used for forming an appropriate seal, as desired.

A sapphire window 454 is disposed over the O-ring 452 and the optical component 432 to separate the interior cavity 444 of the body 428 from an exterior side 456 of the body 428. A threaded cover portion 458 that is complementary to the threaded engagement portion 448 of the body 428 is screwed into the cylindrical recess 450 to engage and compress the sapphire window against the compressible O-ring 452, thereby forming a moisture-proof seal between the interior cavity 444 of the body 428, which contains the IR element 436, leads 440 and other components of the optical component 432, and the exterior side 456 of the body 428. It should be understood that, while the threaded cover portion 458 and the threaded engagement portion 448 threadedly engage each other to form a moisture proof seal, other types of engagement portions, cover portions, and mechanisms may be used. The threaded cover portion 458 forms an aperture 460 over the sapphire window 454 that allows the IR element 436 to emit light toward the exterior side 456 of the body 428 through a gasket hole formed by the O-ring 452, the sapphire window 454, and a cover hole formed by the threaded cover portion 458. In this embodiment, the thin (e.g., 1 mm or less) window 454 is formed from sapphire because of its hardness and durability, and its transparency to IR light, but it should be understood that other materials may be used, as desired. For example, borosilicate may be another suitable material having similar optical properties and biocompatibility to sapphire. In this example, the IR emitter is configured to configured to emit light within a wavelength range of 700 nanometers to 1 millimeter, i.e., the IR wavelength band, and the sapphire window 454 is transparent to some or all of the same IR wavelength band. It should be understood, however, that other light emitters that are configured to emit light in a different predetermined range of light radiation wavelengths may be used.

In this example, the seal formed by the threaded cover portion 458 compressing the O-ring 452 between the sapphire window 454 and the optical component housing 434 forms a cavity seal that atmospherically isolates the cavity 444 from an atmosphere outside the end-effector, i.e., the exterior side 456 of the body 428, while also allowing the cavity 444 to be devoid of potting material. While the threaded cover portion 458 includes outwardly-facing threads that engage with complementary interior-facing threads of the threaded engagement portion 448 of the body 428 in this example, it should be understood that other arrangements are contemplated. For example, a threaded cover portion having inwardly-facing threads may engage with complementary exterior-facing threads of a threaded engagement portion of the body, in some embodiments. Other arrangements may include, in addition or as an alternative, adhesives, friction fit, fasteners, or other arrangements, as desired. In this example, as well, the threaded cover portion 458 includes a chamfered (e.g., 120 degree) interior surface so that the threaded cover portion 458 does not block the visibility of the IR emitter to an end-effector sensor, such as a camera.

Figure 5:
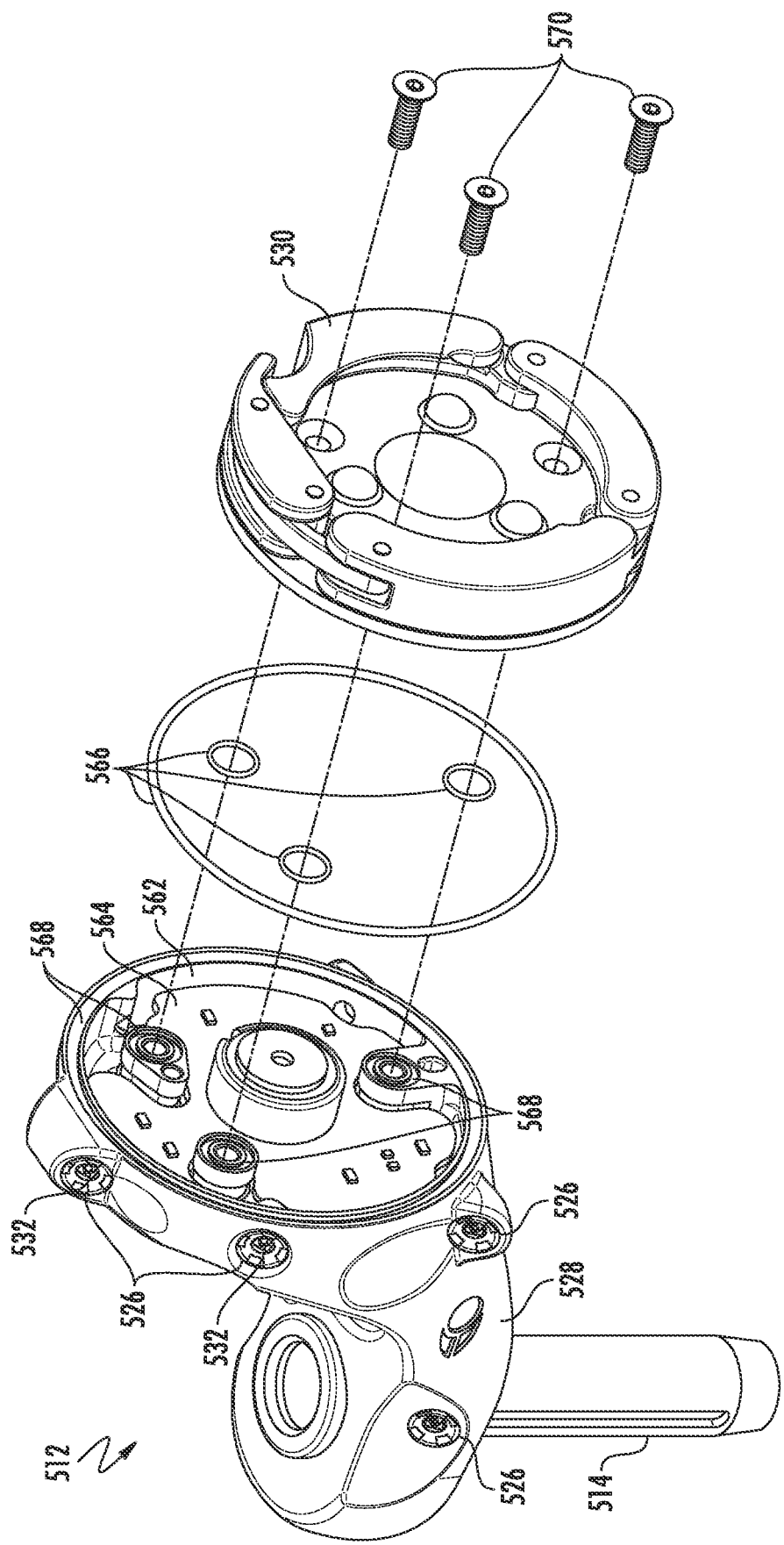
FIG. 5 is an exploded view of an end-effector similar to the end-effector of FIG. 3A illustrating internal components thereof, according to some embodiments.

Referring now to FIG. 5, an exploded view of an end-effector 512 similar to the end-effector 312 of FIG. 3A is illustrated, according to some embodiments. The end-effector 512 in this embodiment forms a guide tube 514 for retaining and/or orienting a surgical instrument, such as the surgical instrument 108 of FIGS. 1 and 2, for example, and also includes a plurality of tracking markers 526 similar to the tracking marker 326, 426 of FIGS. 3A-4B, for example. The end-effector body 528 forms an interior portion 562, with electronic components 564, such as a PCB or other circuitry for controlling the tracking markers 526 and/or other components of the end-effector 512. In this embodiment, a plurality of compressible O-rings 566 are seated in a plurality of complementary O-ring seats 568. The mounting collar 530 is secured to the body 528 of the end-effector 512 to compress the compressible O-rings 566 therebetween, thereby forming moisture-proof seals between the mounting collar 530 and the body 528. In this manner, the entire interior portion 562 of the end-effector 512 may be sealed, thereby protecting the optical components 532 of the tracking markers 526 and the other electronic components 564 of the end-effector 512.

Figure 6A:
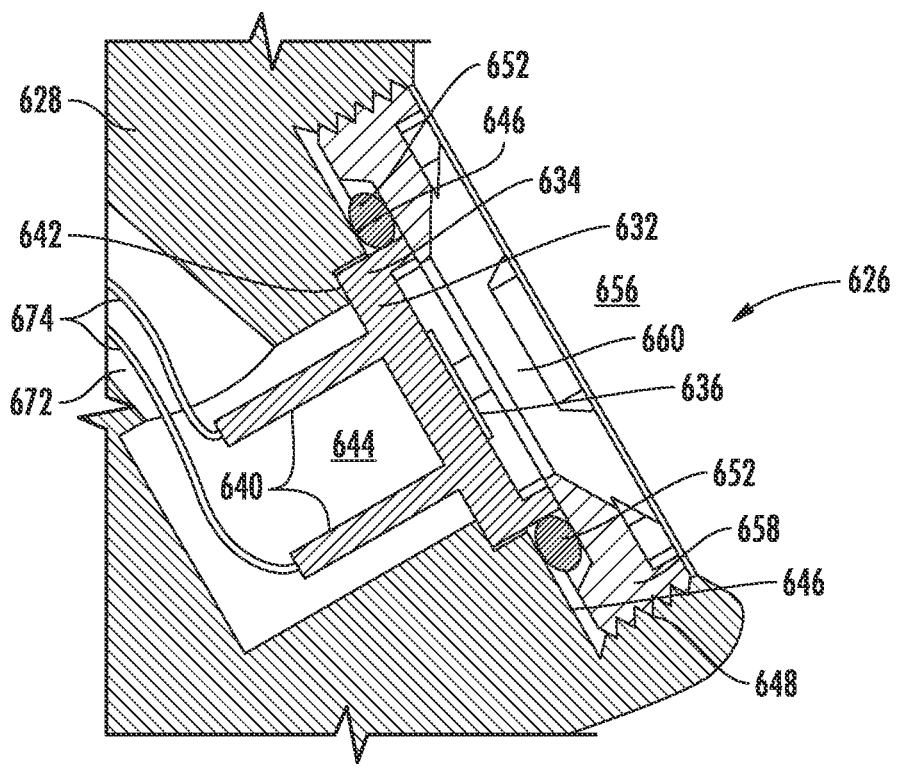
FIGS. 6A and 6B illustrate cross-sectional assembled and exploded views of a windowless mounting arrangement for an optical component similar to the optical component of FIGS. 4A and 4B in an end-effector similar to the end-effector of FIG. 3A, according to some embodiments.
Figure 6B:
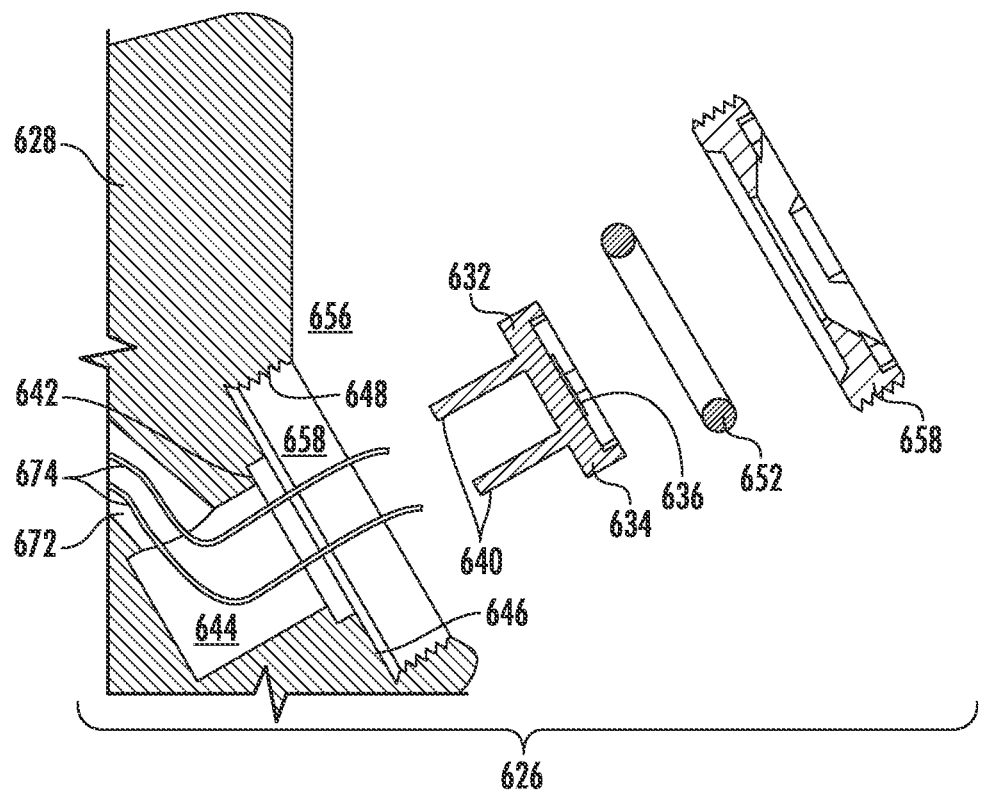

The tracking markers described above, such as the tracking marker 326 of FIGS. 3A and 3B for example, may include a sapphire window that separates the optical component of the tracking marker from an outside environment. It should be understood, however, that a sapphire window or other window may be omitted in some embodiments. For example, in some embodiments, the exterior facing portions of the optical component may be sufficiently durable that a protective window is not necessary. In this regard, FIGS. 6A and 6B illustrate cross-sectional assembled and exploded views of a windowless mounting arrangement for an optical component 632 similar to the optical component of FIGS. 4A and 4B in an end-effector similar to the end-effector 312 of FIG. 3A, according to some embodiments.

In this example, the body 628 includes an optical component seat 642 for receiving and engaging the optical component housing 634 so that the leads 640 of the optical component 632 are disposed on an interior side 644 of the body 628. In this example, the optical component housing 634 includes an O-ring seat 646 for receiving a compressible O-ring 652. The body 630 of the tracking marker 626 also includes a threaded engagement portion 648, which includes inwardly facing threads to form a cylindrical recess 650 in the body 628 of the tracking marker 626 in this example.

To assemble the tracking marker 626, the optical component housing 634 is disposed in the component seat 642 of the body 628 of the tracking marker 626, and a compressible O-ring 652 is disposed around the O-ring seat 646 of the optical component housing 634. A threaded cover portion 658 that is complementary to the threaded engagement portion 648 of the body 628 is screwed into the cylindrical recess 650 to engage and compress the O-ring 652, thereby forming a moisture-proof seal between the interior side 644 of the body 628, which contains the leads 640 and other components of the optical component 632, and the exterior side 656 of the body 628. The threaded cover portion 658 forms an aperture 660 that allows the IR element 636 to emit light toward the exterior side 656 of the body 628. In this embodiment, the IR element 636 may be sufficiently durable that the IR element 636 may be exposed to an exterior environment during use, cleaning and/or sterilization of the end-effector, which may allow for a simplified windowless arrangement, such as the arrangement of FIGS. 6A and 6B.

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belong. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a", "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processor circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s). For example, in some embodiments, a processor circuit may be configured to determine, based on light emitted by one or more light emitters of an optical sub-assembly of an end-effector, a particular one of the plurality of end-effector positions corresponding to a present location of the end-effector. In some embodiments, the wherein the processor circuit is configured to determine a particular one of a plurality of end-effector positions based on the location signal.

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Although several embodiments of inventive concepts have been disclosed in the foregoing specification, it is understood that many modifications and other embodiments of inventive concepts will come to mind to which inventive concepts pertain, having the benefit of teachings presented in the foregoing description and associated drawings. It is thus understood that inventive concepts are not limited to the specific embodiments disclosed hereinabove, and that many modifications and other embodiments are intended to be included within the scope of the appended claims. It is further envisioned that features from one embodiment may be combined or used with the features from a different embodiment(s) described herein. Moreover, although specific terms are employed herein, as well as in the claims which follow, they are used only in a generic and descriptive sense, and not for the purposes of limiting the described inventive concepts, nor the claims which follow. The entire disclosure of each patent and patent publication cited herein is incorporated by reference herein in its entirety, as if each such patent or publication were individually incorporated by reference herein. Various features and/or potential advantages of inventive concepts are set forth in the following claims.

What is claimed is:

1. A ruggedized auto-clavable end-effector for a surgical robot system, comprising:
    an end-effector body configured to guide a surgical instrument and adapted to attach to a robotic arm via a mounting collar, the mounting collar configured to be secured to the end-effector body; the end effector further including:
        an optical sub-assembly received in the end-effector body and including:
            a housing coupled to the end-effector body, the housing comprising an engagement portion;
            a retainer cover engaging the engagement portion of the housing and defining a cover hole therethrough;
            a window that is transparent to a predetermined range of light radiation wave lengths, and being disposed below the retainer cover;
            a gasket disposed below the window and between the end-effector body and the window to define an internal cavity of the end effector body, the gasket further including a gasket hole;
            wherein the retainer cover compresses the gasket between the window and the end effector body to form a seal between the window and the end effector body; and
            a tracking marker disposed in the internal cavity, the tracking marker configured to be tracked by a navigation camera system, the tracking marker configured to emit light through the gasket hole, the window, and the cover hole,
        wherein the mounting collar, when secured to the end effector body is secured to the compress a plurality of O-rings in corresponding O-ring seats to protect the electronic components without any potting material and the optical sub-assembly,
        wherein the retainer cover is threadably engaged to the engagement portion of the housing,
        wherein the seal formed by the retainer cover compressing the gasket between the window and the end effector body forms a cavity seal that atmospherically isolates the internal cavity from an atmosphere outside the end-effector body.

2. The end-effector of claim 1, wherein the window includes a sapphire window.

3. The end-effector of claim 1, wherein the tracking marker is an infrared (IR) emitter, and wherein the predetermined range of light radiation wavelengths is within a wavelength range of 700 nanometers to 1 millimeter.

4. The end-effector of claim 1, wherein the optical sub-assembly comprises a plurality of optical sub-assemblies received in a plurality of recesses in the end effector body.

5. The end-effector of claim 1, wherein the seal formed by the retainer cover compressing the gasket between the window and the end effector body is a moisture-proof seal.

6. The end-effector of claim 1, wherein the seal formed by the retainer cover compressing the gasket between the window and the end effector body forms a cavity seal that atmospherically isolates the internal cavity from an atmosphere outside the end-effector.

7. The end-effector of claim 1, wherein:
the end effector body includes an inwardly facing thread; and
the retainer cover includes an outwardly facing thread that is complementary to the inwardly facing thread of the end effector body.

8. The end-effector of claim 1, wherein:
the retainer cover includes an inwardly facing thread, and
the end effector body includes an outwardly facing thread that is complementary to the inwardly facing thread of the retainer cover.

9. The end-effector of claim 1, wherein the end effector body includes a tube through which the surgical instrument is received.

10. A ruggedized auto-clavable end-effector for a surgical robot system, comprising:
an end-effector body configured to guide a surgical instrument and adapted to attach to a robotic arm, the end effector including:
an optical sub-assembly received in the end-effector body and including:
a window that is transparent to a predetermined range of light radiation wavelengths;
a gasket disposed below the window and between the end-effector body and the window to define an internal cavity of the end effector body, the gasket further including a gasket hole;
a retainer cover disposed over the window and compressing the gasket between the window and the end effector body to form a seal between the window and the end effector body, the retainer cover including a cover hole;
a light emitter disposed in the internal cavity configured to emit light through the gasket hole, the window, and the cover hole; and
a mounting collar, the mounting collar configured to be secured to the end-effector body;
wherein the mounting collar, when secured to the end effector body is secured to the compress a plurality of O-rings in corresponding O-ring seats to protect the electronic components without any potting material and the optical sub-assembly,
wherein an interior portion of the end effector body includes electronic components coupled to the light transmitter and the entire interior portion of the end effector body is free of any potting material,
wherein the retainer cover is threadably engaged to the housing
wherein the seal formed by the retaining cover compressing the gasket between the window and the end effector body forms a cavity seal that atmospherically isolates the internal cavity from an atmosphere outside the end-effector body.

11. The end-effector of claim 10, wherein the O-ring is compressible.

12. The end-effector of claim 10, wherein the window includes a sapphire window.

13. The end-effector of claim 10, wherein the optical sub-assembly comprises a plurality of optical sub-assemblies received in a plurality of recesses in the end effector body.

14. The end-effector of claim 10, wherein:
the end effector body includes an inwardly facing thread; and
the retainer cover includes an outwardly facing thread that is complementary to the inwardly facing thread of the end effector body.

15. The end-effector of claim 10, wherein:
the retainer cover includes an inwardly facing thread, and
the end effector body includes an outwardly facing thread that is complementary to the inwardly facing thread of the retainer cover.

16. The end-effector of claim 10, wherein the end effector body includes a tube through which the surgical instrument is received.

17. The surgical robot system of claim 10, wherein the optical sub-assembly comprises a plurality of optical sub-assemblies, and wherein, for each optical sub-assembly of the plurality of optical sub-assemblies:
the gasket includes a compressible O-ring;
the window includes a sapphire window;
the seal formed by the retainer cover compressing the gasket between the window and the end effector body is a moisture-proof seal and forms a seal that atmospherically isolates the internal cavity from an atmosphere outside the end-effector body; and
wherein the retainer cover includes an outwardly facing thread that is complementary to an inwardly facing thread of the end effector body.

\* \* \* \* \*